US012465301B2

(12) United States Patent
Freudenberger et al.

(10) Patent No.: US 12,465,301 B2
(45) Date of Patent: Nov. 11, 2025

(54) X-RAY SYSTEM AND METHOD FOR OPERATION THEREOF

(71) Applicant: Siemens Healthcare GmbH, Erlangen (DE)

(72) Inventors: Joerg Freudenberger, Kalchreuth (DE); Petra Maurer, Heroldsbach (DE)

(73) Assignee: Siemens Healthineers AG, Forchheim (DE)

( * ) Notice: Subject to any disclaimer, the term of this patent is extended or adjusted under 35 U.S.C. 154(b) by 785 days.

(21) Appl. No.: 16/636,672

(22) PCT Filed: Jul. 31, 2018

(86) PCT No.: PCT/EP2018/070781
§ 371 (c)(1),
(2) Date: Mar. 21, 2023

(87) PCT Pub. No.: WO2019/034417
PCT Pub. Date: Feb. 21, 2019

(65) Prior Publication Data
US 2024/0016458 A1 Jan. 18, 2024

(30) Foreign Application Priority Data
Aug. 15, 2017 (DE) ......................... 102017214196.4

(51) Int. Cl.
*A61B 6/06* (2006.01)
*A61B 6/02* (2006.01)
(Continued)

(52) U.S. Cl.
CPC ................ *A61B 6/06* (2013.01); *A61B 6/025* (2013.01); *A61B 6/4007* (2013.01); *A61B 6/502* (2013.01); *G21K 1/02* (2013.01)

(58) Field of Classification Search
CPC ........... A61B 6/06; A61B 6/08; A61B 6/4021; A61B 6/4035; A61B 6/405; A61B 6/4064;
(Continued)

(56) References Cited

U.S. PATENT DOCUMENTS 4,143,273 A 3/1979 Richey et al.
7,751,528 B2 7/2010 Lalush et al.
(Continued)

FOREIGN PATENT DOCUMENTS

CN 1387449 A 12/2002
CN 101900823 A 12/2010
(Continued)

OTHER PUBLICATIONS

International Search Report and Written Opinion dated Dec. 3, 2018.
German Office Action mailed Jun. 22, 2018.

*Primary Examiner* — Don K Wong
(74) *Attorney, Agent, or Firm* — Harness, Dickey & Pierce, P.L.C.

(57) ABSTRACT

An x-ray system includes an x-ray source which, when in operation, generates x-rays at a plurality of x-ray focal spots, with a collimator allocated in each case to each x-ray focal spot. The collimator selects x-rays generated in the respective x-ray focal spot and directed onto a common detector, collimators being in a fixed position in relation to the respective allocated x-ray focal spots. The x-ray source is embodied as an x-ray tube with at least one anode including the x-ray focal spots and with a plurality of cathodes. Or the x-ray source includes a plurality of x-ray tubes, the anodes whereof include the x-ray focal spots. The collimators are arranged in the respective x-ray tube, and the collimators are
(Continued)

arranged on the respective anode. A method is further for operating such an x-ray system.

20 Claims, 4 Drawing Sheets

(51) Int. Cl.
*A61B 6/40* (2024.01)
*A61B 6/50* (2024.01)
*G21K 1/02* (2006.01)

(58) Field of Classification Search
CPC ....... A61B 6/40; A61B 6/4007; A61B 6/4014; H05G 1/52; H05G 1/00
See application file for complete search history.

(56) References Cited

U.S. PATENT DOCUMENTS

| | | | |
|---|---|---|---|
| 9,502,148 | B2 | 11/2016 | Ren et al. |
| 2005/0245819 | A1 | 11/2005 | Kumakhov |
| 2010/0091940 | A1 | 4/2010 | Ludwig et al. |
| 2011/0286581 | A1 | 11/2011 | Sprenger et al. |
| 2012/0134463 | A1 | 5/2012 | Kaneko |
| 2012/0195403 | A1 | 8/2012 | Karellas et al. |
| 2014/0112449 | A1 | 4/2014 | Zou et al. |
| 2015/0359504 | A1 | 12/2015 | Zhou et al. |
| 2017/0181716 | A1 | 6/2017 | Koehler et al. |

FOREIGN PATENT DOCUMENTS

| | | | | |
|---|---|---|---|---|
| CN | 102680501 | A | 9/2012 | |
| CN | 102870189 | A | 1/2013 | |
| CN | 103077875 | A | 5/2013 | |
| CN | 103385732 | A | 11/2013 | |
| CN | 106535770 | A | 3/2017 | |
| DE | 102008046722 | A1 | 3/2010 | |
| DE | 102008050571 | A1 | 4/2010 | |
| WO | WO 2006130630 | A2 | 12/2006 | |
| WO | WO 2014116665 | A2 | 7/2014 | |
| WO | WO 2015132593 | A1 | 9/2015 | |
| WO | WO-2015173750 | A1 * | 11/2015 | ............ A61B 6/032 |
| WO | WO 2017130013 | A1 | 8/2017 | |

* cited by examiner

X-RAY SYSTEM AND METHOD FOR OPERATION THEREOF

PRIORITY STATEMENT

This application is the national phase under 35 U.S.C. 371 of PCT International Application No. PCT/EP2018/070781 which has an International filing date of Jul. 31, 2018, which designated the United States of America and which claims priority to German patent application no. DE 102017214196.4 filed Aug. 15, 2017, the entire contents of each of which are hereby incorporated herein by reference.

FIELD

Embodiments of the invention generally relate to an x-ray system with an x-ray source which, when in operation, generates x-rays at a plurality of x-ray focal spots with a collimator being allocated in each case to each x-ray focal spot. Embodiments further relate to a method for operating such an x-ray system.

BACKGROUND

X-ray systems are used in medical examinations. Here, x-rays are generated in an x-ray focal spot of an x-ray source and emitted therefrom. The x-rays subsequently penetrate an object to be examined, wherein at least part of the x-rays are absorbed by the object, and the x-rays generate an x-ray image on a, in particular digital, detector. If a plurality of x-ray images of the object (projections) are acquired from different spatial angles (projection angles), a three-dimensional reconstruction of the object can be drawn up from the projections via an appropriate algorithm and image data can be generated therefrom. Advantageously, it is possible in this way to achieve improved differentiation and location of structures in the object that, due to their position in relation to one another, for example, lead in an individual imaging shot to an x-ray image that is only comparatively unclear to decipher. For example, in mammography using what is known as tomosynthesis, as against a conventional two-dimensional mammogram of the breast, a tumor can advantageously be more easily distinguished from the overlying or underlying tissue, which is how misdiagnoses can be avoided.

In tomosynthesis, a plurality of projections of the object are recorded at a projection angle of the object that differs in each case, in a limited angular range, which is, for example, between 10° and 50°. For this purpose, a relative orientation of the detector, of the object and of an x-ray focal spot in the x-ray source are changed in relation to one another. For example, both the detector and the x-ray source are moved in relation to each other in a given manner. Alternatively, the detector is in a fixed position and only the x-ray source is moved, or the x-ray source is in a fixed position and only the detector is moved.

U.S. Pat. No. 7,751,528 discloses a further option, in which the x-ray system has a detector that is in a fixed position and the x-ray source is not moved mechanically. Here the x-ray source has a plurality of x-ray focal spots in a fixed position, said focal spots being activated sequentially one after the other and emitting x-rays. The x-ray focal spots are locally distributed such that appropriate projections can be generated for reconstructing the object. Therefore, the x-ray focal spots are arranged on a line running parallel to the detector, for example.

When recording the projections, the x-rays emitted from the or from each x-ray focal spot are collimated via a collimator or collimated onto the detector via a collimator in each case. In other words, those x-rays that are not directed at the detector are suppressed via the collimator. In this way, in particular, during mammography, the exposure of a person to be examined (a patient) to radiation that is not required for imaging can be avoided and the patient's exposure to radiation is reduced.

The time required for an examination needs to be kept as short as possible. In this way, a motion blur of the person to be examined is reduced when recording the projections. In addition, during mammography for example, an examination that is uncomfortable or painful for the person to be examined is shortened.

For example, the x-ray source and/or the collimator are/is displaced during the examination to record the projections, such that a comparatively large amount of time passes that is not used to record the projections. As a result, the time required for the examination is comparatively long, such that the motion blur and/or a discomfort for the person to be examined is comparatively great.

WO 2014/116665 A2 discloses a system suitable for tomosynthesis, comprising a plurality of x-ray focal spots, in which the x-rays emitted from an x-ray focal spot are collimated via a common collimator or via a collimator in each case. The x-ray source and/or the collimator or collimators are adjustably arranged and embodied, for example rotatably or movably, such that an imaging geometry can be adjusted to suit a planned examination. For this, the x-ray source and the collimator or collimators must be controlled accordingly, and the system must have an adjustment apparatus suitable for making the adjustment.

Furthermore, WO 2015/132593 A1 discloses a collimator, comprising a substrate containing a plurality of holes, each hole being frustoconical at one end and tubular at the other end for use in an x-ray imaging system. In addition, the x-ray collimator is aligned with a two-dimensional array of x-ray sources and a two-dimensional x-ray sensor.

WO 2017/130013 A1 discloses a system with an emitter array comprising a plurality of emitters for generating x-rays. Here, a collimator is used to limit an emission angle in the respective emitter. For this purpose, a plate made from air-tight material in which a number of holes of appropriate size have been drilled is used.

DE 10 2008 050 571 A1 discloses a tomosynthesis device comprising a multi-focus x-ray source with a plurality of x-ray emitters, each of which is suitable for generating a beam of x-rays. Here, each x-ray emitter is allocated a collimator, which is located in the beam path between the x-ray focus of the x-ray emitter and a detector.

SUMMARY

At least one embodiment of the invention addresses a problem of providing a particularly suitable x-ray system, in which the duration of the examination is as short as possible and/or which has a design that is as simple as possible. Furthermore, a suitable method for operating such an x-ray system is provided in at least one embodiment.

Embodiments of the invention are directed to an x-ray system and a method. Advantageous embodiments and further developments form the subject of the claims.

The x-ray system of at least one embodiment comprises an x-ray source that, when in operation, generates x-rays at a plurality of x-ray focal spots. Each x-ray focal spot is allocated a collimator, which selects the x-rays generated in the respective x-ray focal spot and directed onto a common detector. In other words, the x-rays emitted from the x-ray focal spots are collimated onto the detector that is common to all the x-ray focal spots via the collimator allocated in each case. The collimators are fixed in position in relation to the respective allocated x-ray focal spot. In other words, a relative position between the x-ray focal spot and the collimator is chronologically constant.

BRIEF DESCRIPTION OF THE DRAWINGS

The example embodiments of the invention are described hereinafter in greater detail with reference to the drawing. The drawing shows.

Figure 1:
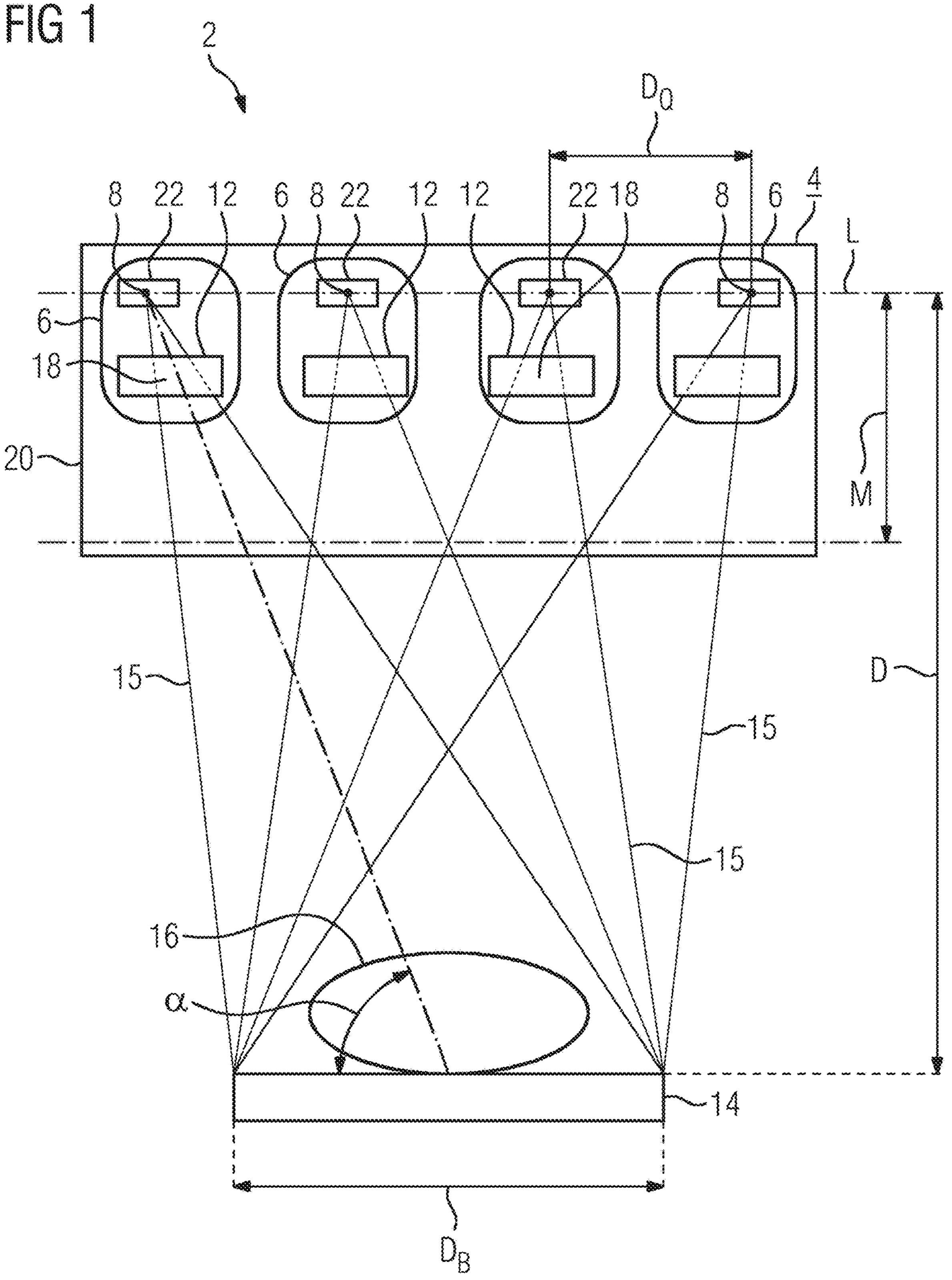
FIG. 1 in diagram form, an x-ray system with an x-ray source with a plurality of x-ray tubes, each with an x-ray focal spot, wherein the x-rays emitted from the x-ray focal spots are collimated onto a detector via a collimator allocated to the respective x-ray focal spot, and wherein the x-rays penetrate an object at a projection angle, FIG. 2 in diagram form, the x-ray system with an alternative embodiment of the x-ray source, wherein the x-ray source is embodied as an x-ray tube with an anode comprising the x-ray focal spots and shaped as a circular arc, and wherein the collimators are designed to connect and are arranged inside the x-ray tube, FIG. 3 in diagram form, an alternative embodiment of the x-ray tube according to FIG. 2 in a cross section through an x-ray focal spot, with a cathode and with a collimator and also with the anode, the collimator being attached to the anode, FIG. 4 an alternative design of the x-ray tube according to FIG. 3, in which the collimator is attached to the vacuum casing of the x-ray tube.

Components that are equivalent to one another are denoted by the same reference signs in all the figures.

DETAILED DESCRIPTION OF THE EXAMPLE EMBODIMENTS

The x-ray system of at least one embodiment comprises an x-ray source that, when in operation, generates x-rays at a plurality of x-ray focal spots. Each x-ray focal spot is allocated a collimator, which selects the x-rays generated in the respective x-ray focal spot and directed onto a common detector. In other words, the x-rays emitted from the x-ray focal spots are collimated onto the detector that is common to all the x-ray focal spots via the collimator allocated in each case. The collimators are fixed in position in relation to the respective allocated x-ray focal spot. In other words, a relative position between the x-ray focal spot and the collimator is chronologically constant.

The x-rays beamed (emitted) from one of the x-ray focal spots penetrate an object arranged between the x-ray focal spot in the x-ray source and the detector in a (projection) angle, which is determined for example, in relation to an orientation of the detector or preferably of the object. The x-rays are acquired via the detector. In this way, a (projection) x-ray image is recorded via the detector. For three-dimensional reconstruction and hence for preparing image data from the reconstruction, at least two different projections are recorded from an object, preferably a number of different projections that is equivalent to the number of x-ray focal spots. In other words, at least two x-ray images recorded at different projection angles are required for the reconstruction.

When operating the x-ray system, the x-rays are generated in the x-ray focal spots. The x-ray focal spots in the x-ray system are spatially distributed in the x-ray source. In particular, the x-ray focal spots are arranged apart from one another, that is, in each case the x-ray focal spots do not overlap either partly or completely. The x-ray source locations are preferably the same size, and the x-ray focal spots are preferably arranged at regular intervals on a line or on an area.

For example, the x-ray focal spots are equidistant along a straight line that runs parallel to the detector. Alternatively, the x-ray focal spots are arranged along a section of a circular arc, said circular arc defining a plane that is perpendicular to the detector. In a further alternative, the x-ray focal spots are matrix-shaped, that is, arranged in a grid-like manner on a flat or essentially spherical area. Due to the regular arrangement thereof, in particular a three-dimensional reconstruction of the object is simplified.

Due to the spatial distribution of the x-ray focal spots, projections of the object are recorded from different projection angles. Unlike x-ray systems that have only one single x-ray focal spot, in this way, the recording of the projections at different projection angles is facilitated without the x-ray source and hence the x-ray focal spot having to be displaced, for example, moved or swiveled.

The detector is designed to acquire (detect) the x-rays emitted by the x-ray source, that is, the detector is sensitive to electromagnetic radiation in a wavelength range equivalent to the x-rays emitted. In particular, the detector is a digital detector, for example, a flat image detector for x-rays (a solid-state detector) or a detector comprising a scintillator and a camera.

The x-ray source is controlled via a control device, in particular such that the x-rays are emitted in a chronological sequence, that is sequentially, from the corresponding x-ray focal spots. For example, the detector is likewise activated via the control device such that the recording of a projection ensues via the detector synchronous with (at the same time or time-correlated) with the exposure thereof to the x-rays that have been emitted.

The collimators are formed from a material that absorbs x-rays as effectively as possible. For example, the collimators are manufactured from lead, tungsten or brass. Furthermore, the collimators are shaped or geometrically designed such that in each case the x-rays emitted from each x-ray focal spot allocated to the collimator are or become collimated onto the detector. In other words, in each case, the part of the x-rays emitted from the x-ray focal spot that would not impinge on the detector without taking into account the interaction of the x-rays with the object is absorbed by the collimator. The collimator is usefully arranged between the allocated x-ray focal spot and the detector. Insofar as the object to be examined is located between the x-ray focal spot and the detector, the collimator is arranged between the x-ray focal spot and the object.

For example, the collimators are designed to be connected, in one piece, or as a monobloc. According to a preferred embodiment, however, the collimators are designed to be a separate component in each case. Unlike the embodiment that is connected, in this way in particular, an individual adjustment of the individual collimators is advantageously facilitated in the assembly thereof.

Due to the fixed arrangement of the collimators in relation to the respective x-ray focal spot and insofar as the detector is fixed in position in relation to the x-ray focal spot, in particular for the duration of an examination to record the projections, it is facilitated according to an appropriate embodiment that in each case a collimator has only one slot, running continuously from the side thereof that faces the x-ray focal spot to the side thereof that faces the detector, which slot is penetrated unimpeded by the x-rays when the x-ray system is in operation. In particular, the detector has a rectangular detector area, such that the slot is usefully designed in the shape of a truncated pyramid. The collimator therefore does not comprise any covers or other adjustable elements, which is why, advantageously, a control unit is not required for the collimators. In other words, the collimator has a rigid design. To sum up, a particularly simple design of the collimator has been achieved.

Due to the collimation of the x-rays onto the detector, the object, such as, for example, a part of the body of the patient who is to be examined, is penetrated only by that part of the x-rays emitted from the x-ray focal spots that contributes to the recording of a projection via the detector. Therefore, the exposure to radiation of the person to be examined is particularly low. Furthermore, particularly advantageously, the duration of the examination required to record the projections is comparatively short due to the fixed arrangement of the collimators in relation to the respective x-ray focal spots.

At least one embodiment of the invention takes as its point of departure the consideration that follows, namely that in an x-ray system which has only one x-ray focal spot, in the examination of the object to record the projections at different projection angles, both the x-ray source and the collimator would have to be adjusted accordingly. In x-ray systems with a plurality of x-ray focal spots, it is not necessary to displace the x-ray source to record the projections. However, insofar as the collimators are not in a fixed position in relation to the respective x-ray focal spot allocated thereto, and/or insofar as a dedicated collimator is not allocated to every x-ray focal spot, during the examination, the collimators are adjusted in each case for the collimation of the x-rays emitted from an x-ray focal spot onto the detector. This adjustment is comparatively time-intensive, with in particular the time required for the adjustment (adjustment time) being comparatively long compared with a read-out time for the detector. As a result, the time between the recording of two projections with different projection angles is essentially determined by the time required for the adjustment. On the other hand, if the collimators are fixed, this comparatively long adjustment time is eliminated, which is why the duration of the examination is advantageously shortened.

Furthermore, the x-ray source is embodied as an x-ray tube comprising an anode and a number of cathodes. In other words, the anode and the cathodes are enclosed by a common vacuum casing that forms the x-ray tube. According to a useful design, the number of cathodes is equal to the number of x-ray focal spots, such that an x-ray focal spot is generated in each case via an anode. An x-ray focal spot is therefore understood to be that area of the anode in which electrons emitted by the corresponding cathode interact with the anode and in this way x-rays are generated. Alternatively, the x-ray tube comprises a plurality of anodes which, for example, each have an x-ray focal spot or alternatively each comprise a plurality of the x-ray focal spots.

In an alternative embodiment, the x-ray source comprises a plurality of x-ray tubes. Here for example, the x-ray tubes each have an anode with an x-ray focal spot or alternatively an anode with a plurality of x-ray focal spots or a plurality of anodes each having an x-ray focal spot or a plurality of anodes with a plurality of x-ray focal spots.

In any case, the x-ray focal spots are arranged such that they are spatially distributed in an appropriate manner to record the projections at different projection angles.

The x-ray source is usefully arranged in an X-ray emitter housing. The X-ray emitter housing covers the x-ray source and also for example, electronics for the x-ray system.

In order to facilitate a fixed arrangement of the respective collimators allocated thereto in relation to the x-ray focal spots and hence a comparatively simple design of the collimators without adjustable elements, for example, the detector has to be in a fixed position for recording the projections in relation to the x-ray focal spots, at least for the duration of the examination. In addition, in each case, the collimator for an allocated x-ray focal spot must always be arranged outside that spatial region that is penetrated by x-rays collimated onto the detector from the other x-ray focal spots, that is, without displacing said focal spot. This is facilitated in a comparatively close arrangement of the collimator on the corresponding x-ray focal spots. Here a maximum distance of the collimator from the line or from the area on which the x-ray focal spots are arranged emerges in each case, at which distance a fixed arrangement of the collimator is facilitated in relation to the allocated x-ray source point. Said point is dependent in particular on the distance of the x-ray focal spot from an adjacent x-ray focal spot, on the width of the detector and on the distance of the detector from the line or from the area on which the x-ray focal spots are arranged.

For this purpose, the collimators are arranged in the x-ray tube, or where the x-ray source is designed with a plurality of x-ray tubes, arranged in the respective x-ray tube. In other words, the collimators are arranged in that x-ray tube in which the x-ray focal spot allocated to the collimator is arranged. As a result, the collimators are arranged sufficiently close to the allocated x-ray focal spots, that is, the collimators have in each case a distance from the line or the area on which the x-ray focal spots are arranged that is less than the maximum distance. Therefore, the collimators are advantageously arrangeable and also arranged in a fixed position in relation to the allocated x-ray focal spot.

To sum up, the collimators have to be arranged such that the collimators have a distance from the line or the area on which the x-ray focal spots are arranged that is less than the maximum distance in order to facilitate an arrangement that is fixed in relation to the x-ray focal spots. In particular, due to this maximum distance, the collimators are arranged inside the x-ray tube, that is, inside the or each x-ray tube, and consequently inside the X-ray emitter housing.

The collimators are arranged on the anode. In an embodiment of the x-ray source with a plurality of anodes, the collimators are arranged accordingly on the anodes. As a result, the collimators are at a relatively short distance from the respective allocated x-ray focal spot, such that the collimators are advantageously in a fixed position.

In particular, the collimators are attached onto the anode via an additive method. For example, the collimators are printed onto the intended locations via a 3D-printing process. Alternatively, the collimators are manufactured in each case before their assembly by milling or turning and subsequently attached to the intended locations on the anode, for example, soldered, welded, pinned or firmly bonded (glued).

According to an advantageous embodiment, an x-ray system embodied according to one of the variants described in the aforementioned is used in tomosynthesis, in particular in mammography, to generate image data. The x-ray system embodied in this way has a comparatively simple design due to the fixed collimators. Furthermore, the duration of the examination of an object via this x-ray system, in particular of a human breast in a patient in the case of mammography, is advantageously comparatively short, which is how any motion blur caused by the patient is reduced and/or an examination that is uncomfortable or painful for the patient is shortened.

FIG. 1 shows an x-ray system 2 with an x-ray source 4, which comprises a plurality of x-ray tubes 6 where, for purposes of improved clarity, only four x-ray tubes 6 are shown. When in operation, the x-ray tubes 6 are activated sequentially via a control device that is not further shown, that is, activated in chronological sequence, such that x-rays 10 (FIG. 3 and FIG. 4) are emitted at one time only from one x-ray focal spot 8 arranged in the x-ray tube.

The x-rays 10 emitted from an x-ray focal spot 8 are collimated, in each case via a collimator 12, onto a detector 14 having a detector width DB, which detector is in a fixed position in relation to the x-ray focal spots 8. In other words, those x-rays 10 that are not directed onto the detector via the collimator 12 that is allocated to the appropriate x-ray focal spot 8 are suppressed.

The x-rays 10 directed onto the detector 14 are shown collectively as a beam 15. To sum up, via the collimator 12, those x-rays 10 emitted from the x-ray focal spot 8 thereof that are directed onto the detector 14 are selected. As a result, the part of the x-rays 10 that does not contribute to a projection of an object 16 is absorbed by the respective allocated collimator 12.

Via the x-ray system 2, a plurality of projections are created at a projection angle α, said projections being used for the three-dimensional reconstruction of the object 16 and for the acquisition of image data from this reconstruction via an evaluation unit that is not shown in further detail. The projection angle α is determined here from the position of the respective x-ray focal spot 8 in relation to the object 16. For purposes of improved clarity, only one projection angle α corresponding to an x-ray focal spot 8 is marked.

As shown in FIG. 1, the detector 14 and also the x-ray source 4 are in a fixed position, such that an angular range of the projection angle α is limited as a result thereof. A three-dimensional reconstruction of an object 16 via the projections recorded from a limited angular range is henceforth referred to as tomosynthesis. To sum up, the x-ray system 2 is therefore used in tomosynthesis, in particular in mammography, for generating image data from a three-dimensional reconstruction of the object 16.

The x-ray focal spots 8 are arranged equidistantly on a straight line L parallel to the detector 14 and spaced apart, which is an appropriate arrangement for the reconstruction. The x-ray focal spots 8 are at a distance DQ from the respective adjacent x-ray focal spot 8, and the line L is at a distance D from the detector 14.

Advantageously, the collimators 12 are fixed in position in relation to their respective allocated x-ray focal spot 8. In other words, the collimators 12 are not adjustable or movable. A collimator 12 is therefore in each case arranged in an area that is not penetrated by the collimated beams 15 from the other x-ray focal spots 8. In this way, the collimators 12 are fixed in position in relation to their respective allocated x-ray focal spot 8, without limiting the beam 15 from the other x-ray focal spots 8 that is collimated onto the detector 14. For this purpose, the collimators may be no further than a maximum distance M apart from the line L. The following equation applies to the maximum distance M: M=D*DQ/(DB+DQ).

Due to the fixed arrangement of the collimators 12, a simple design of the collimators 12 and also of the x-ray system 2 is provided. The collimators 12 each have only one slot 18, which extends continuously from the side of the respective collimator 12 that faces the x-ray focal spot 8 to the side of the respective collimator 12 that faces the detector 14. The collimators 12 do not therefore have any adjustable elements, such as for example, adjustable covers. In other words, the collimators 12 are rigid in design.

To sum up, the collimators 12 are neither adjustable, nor do the collimators 12 comprise any adjustable elements, such that neither is an adjustment device necessary for the collimators 12 nor is a corresponding control unit necessary for them. In addition, due to this, the time necessary for adjustment is eliminated such that the total duration of the tomosynthesis is shortened.

In FIG. 1 the collimators 14 are arranged inside the x-ray tube 6 that encloses the respective allocated x-ray focal spot 8, and consequently are no further apart than the maximum distance M from the line L. The x-ray source 4 and hence the x-ray tubes 6 are arranged in a common X-ray emitter housing 20. Here, the X-ray emitter housing 20 includes further elements that are not shown, for example, electronics.

Figure 2:
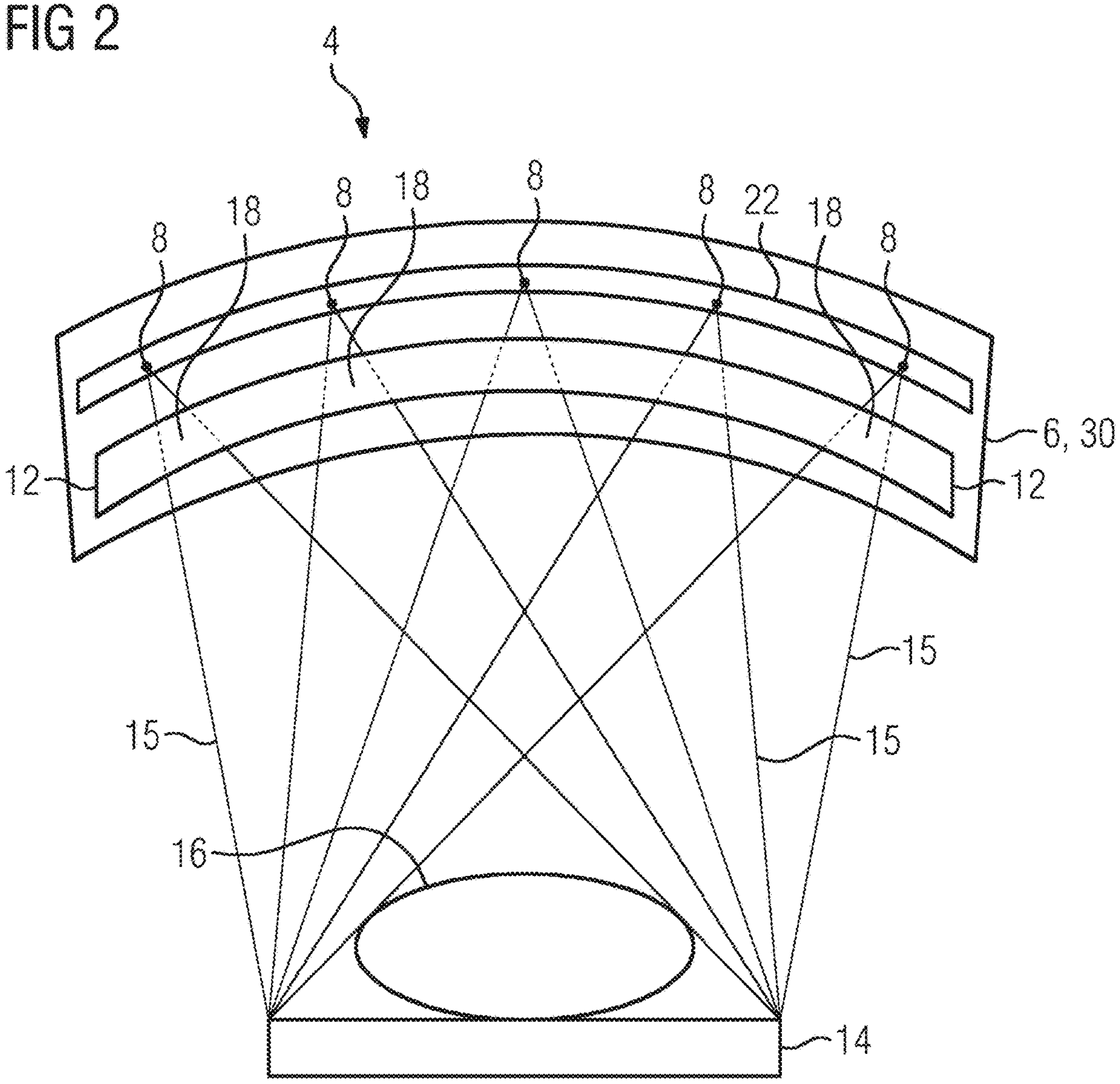
Figure 3:
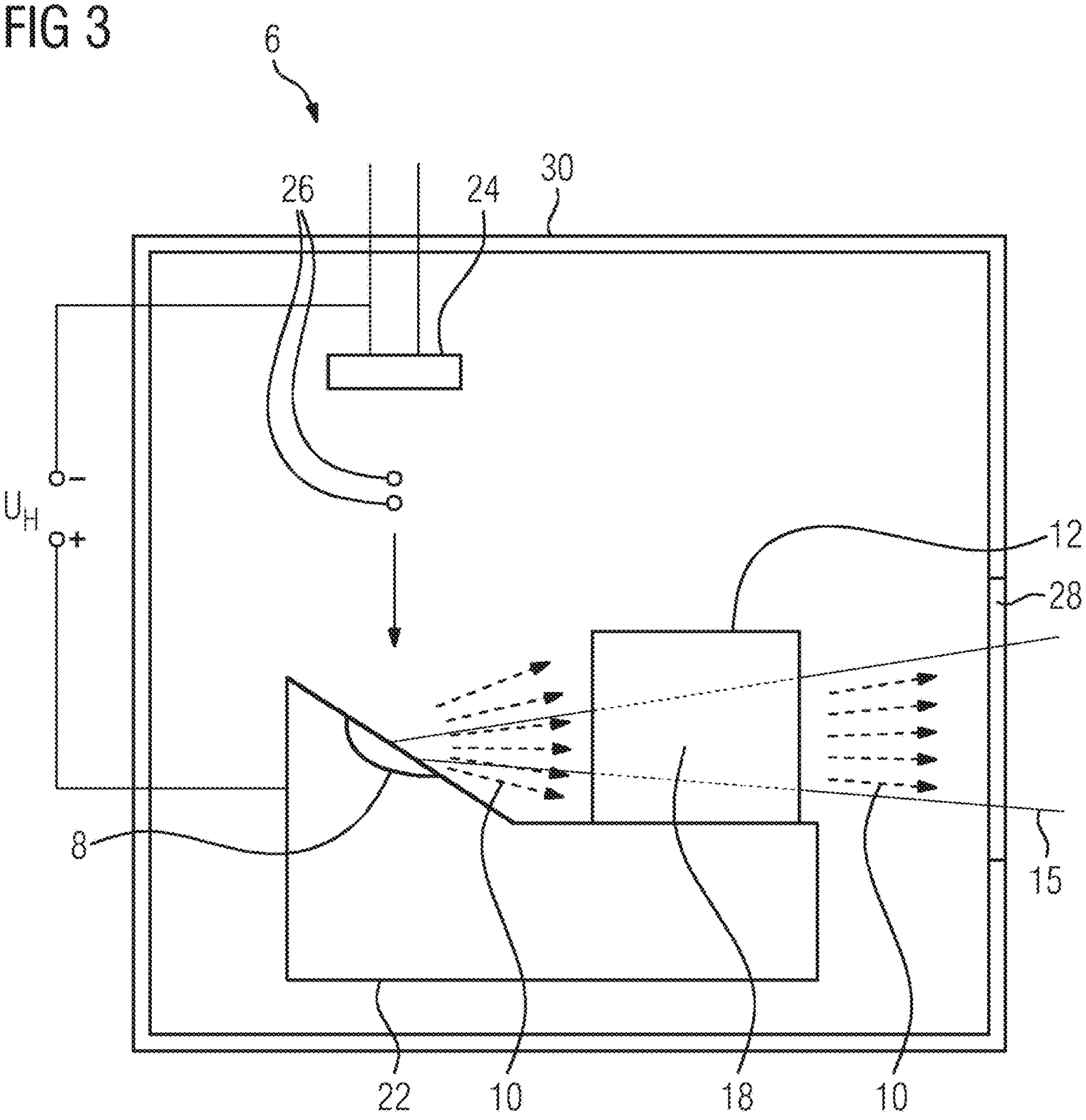
Figure 4:
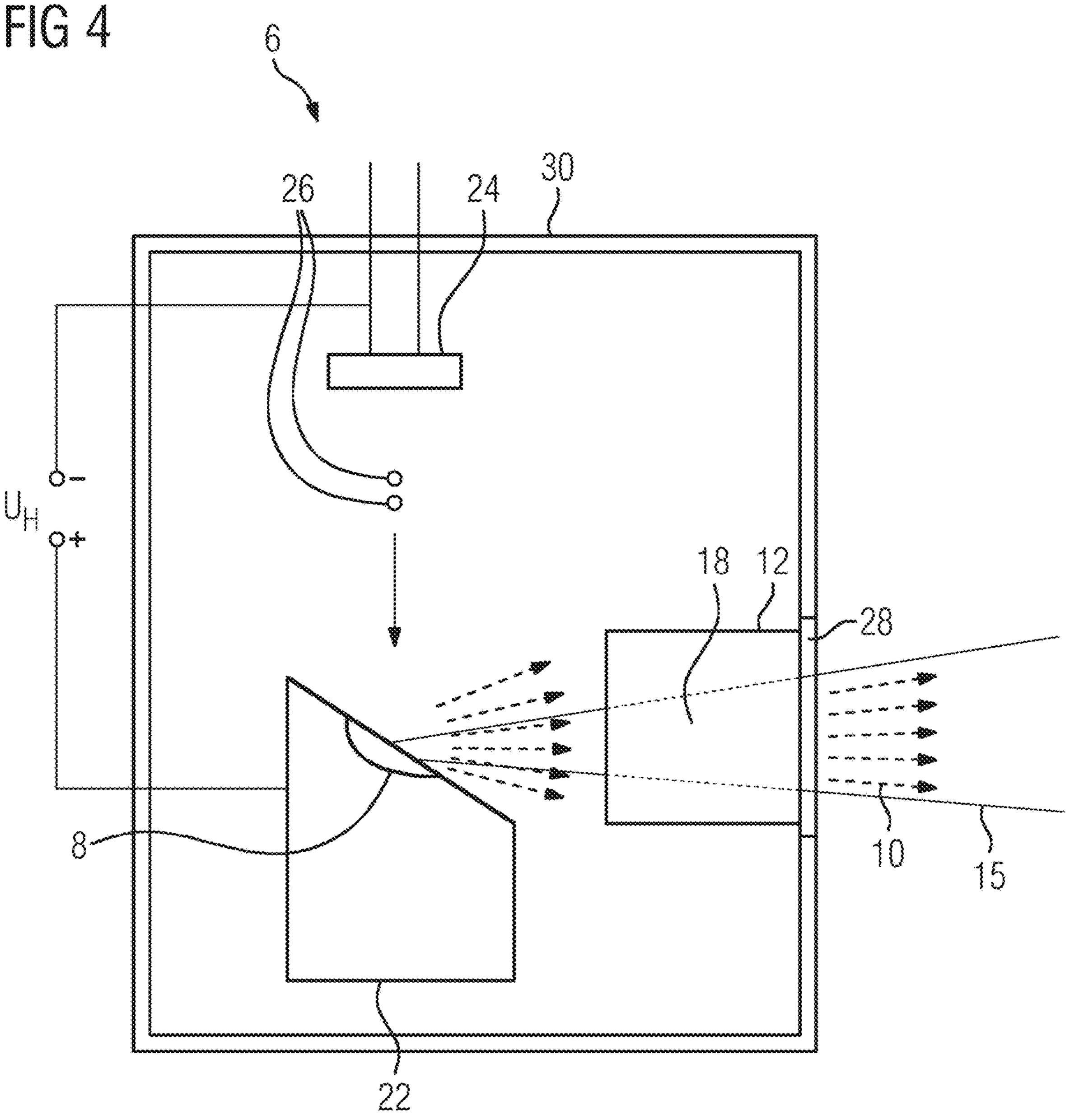

FIG. 2 shows the x-ray system 2 with an alternative design of the x-ray source 4. Said source has one single x-ray tube 6 with an anode 22, on which, in operation, the x-ray focal spots 8 are generated sequentially using one allocated cathode 24 in each case (FIG. 3 and FIG. 4). Here the line L, on which the x-ray focal spots 8 are arranged, is in the form of a circular arc. Furthermore, the collimators 12 are arranged inside the x-ray tube 6, the collimators 12 being designed to be connected. In other words, the collimators 12 are designed as an element comprising a number of x-ray focal spots 8 equivalent to the number of slots 18. The collimators 12 are fixed in position in relation to the anode 22, with the collimators 12 being attached to a support element that is not further shown. This element facilitates the adjustment of the collimator 12 when assembling the x-ray system 2 before it goes into operation.

FIG. 3 shows an alternative embodiment of the x-ray tube 6 according to FIG. 2 in a cross section through an x-ray focal spot 8, with a viewing direction along the line L. It shows only the cathode 24 that is arranged in the intersection plane, and the collimator 12 that is arranged in the intersection plane. However, a number of cathodes 24 equivalent to the number of x-ray focal spots 8 are arranged in the x-ray tube 6. An x-ray focal spot 8 is created in each case on the cathode 24.

For this purpose, electrons 26 emitted from the cathode 24 are sped towards the anode 22 via a high voltage UH established between the cathode 24 and the anode 22. These subsequently interact in the x-ray focal spot 8 of the anode 22, generating the x-rays 10 with the anode 22. The beam 15 of the collimated x-rays 10 penetrates a window 28, which is transparent to x-rays 10, in the vacuum casing 30 that encloses the x-ray tube 6 towards the outside of the x-ray tube 6.

Unlike the embodiment according to FIG. 2, the collimator 12 is incorporated into the anode 22. In particular, the collimator 12 is attached to the anode 22 via an additive method, for example, via a 3D-printing process. In this way, the collimators 12 are fixed in position in relation to their respective allocated x-ray focal spots 8.

FIG. 4 shows an alternative embodiment of the x-ray tube 6 in cross section. In a similar manner to FIG. 3, the x-ray tube comprises the anode 22 and also the cathodes 24 for generating the x-rays 10 in the corresponding x-ray focal spots 8. Here, the collimator 12 is attached on the inside of the x-ray tube 6 in the area of the window 28 to the vacuum casing 30 of the x-ray tube 6. As a result, the collimator 12 is fixed in position in relation to its allocated x-ray focal spot 8.

The statements relating to FIGS. 3 and 4 also apply in a similar way to the x-ray tubes 6 according to FIG. 1. The collimators 12 are therefore inside the respective x-ray tube 6 on the corresponding anode 22 or attached inside the respective x-ray tube 6 to its vacuum casing 30 in the area of the window 28 in the vacuum casing 30.

The invention is not restricted to the example embodiments described in the aforementioned. In fact, it is also possible for other variants of the invention to also be derived therefrom by a person skilled in the art without departing from the subject matter of the invention. In particular, all the individual features described in connection with the example embodiments can also be combined with one another in a different way without departing from the subject matter of the invention.

The invention claimed is:

1. An x-ray system, comprising:

an x-ray source to generate first x-rays at a plurality of x-ray focal spots; and a plurality of collimators, each respective collimator among the plurality of collimators being allocated to a corresponding x-ray focal spot among the plurality of x-ray focal spots, configured to select second x-rays generated in the corresponding x-ray focal spot, the second x-rays being a set of the first x-rays, the second x-rays being and directed onto a common detector, and in a fixed position in relation to the corresponding x-ray focal spot, wherein the x-ray source is embodied as a first x-ray tube including at least one anode and a plurality of cathodes, the at least one anode including the plurality of x-ray focal spots, the plurality of collimators being in the first x-ray tube, or includes a plurality of x-ray tubes, anodes of the plurality of x-ray tubes including the plurality of x-ray focal spots, and each respective collimator being in a corresponding x-ray tube among the plurality of x-ray tubes.

2. The x-ray system of claim 1, wherein the plurality of collimators are rigid.

3. The x-ray system of claim 1, wherein the x-ray source is embodied as the first x-ray tube, the plurality of collimators being on the at least one anode in the first x-ray tube; or the x-ray source is embodied as the plurality of x-ray tubes, each respective collimator among the plurality of collimators being on a corresponding anodes in a corresponding x-ray tube among the plurality of x-ray tubes, and the corresponding anode being among the anodes.

4. The x-ray system of claim 1, wherein the x-ray source is embodied as the first x-ray tube, the plurality of collimators being attached to an inside of a vacuum casing of the first x-ray tube; or the x-ray source is embodied as the plurality of x-ray tubes, each respective collimator among the plurality of collimators being attached to an inside of a vacuum casing of a corresponding x-ray tube among the plurality of x-ray tubes.

5. The x-ray system of claim 1, wherein a number of the plurality of cathodes is equal to a number of the plurality of x-ray focal spots.

6. The x-ray system of claim 1, wherein each of the plurality of collimators is separate from one another.

7. A method of using an x-ray system, the x-ray system including an x-ray source to generate first x-rays at a plurality of x-ray focal spots, and a plurality of collimators, each respective collimator among the plurality of collimators being allocated to a corresponding x-ray focal spot among the plurality of x-ray focal spots, configured to select second x-rays generated in the corresponding x-ray focal spot, the second x-rays being a set of the first x-rays, and the second x-rays being directed onto a common detector, in a fixed position in relation to the corresponding x-ray focal spots, wherein the x-ray source is embodied as a first x-ray tube including at least one anode and a plurality of cathodes, the at least one anode including the plurality of x-ray focal spots, and the plurality of collimators being on the at least one anode in the first x-ray tube, or includes a plurality of x-ray tubes, anodes of the plurality of x-ray tubes including the plurality of x-ray focal spots, each respective collimators among the plurality of collimators being on a corresponding anode in a corresponding x-ray tube among the plurality of x-ray tubes, and the corresponding anode being among the anodes, the method comprising:

generating image data in tomosynthesis using the x-ray system.

8. A method for operating an x-ray system, the x-ray system including an x-ray source to generate first x-rays at a plurality of x-ray focal spots, and a plurality of collimators, each respective collimator among the plurality of collimators being allocated to a corresponding x-ray focal spot among the plurality of x-ray focal spots, configured to select second x-rays generated in the corresponding x-ray focal spot, the second x-rays being a set of the first x-rays, and the second x-rays being directed onto a common detector, in a fixed position in relation to the corresponding x-ray focal spot, wherein the x-ray source is embodied as a first x-ray tube including at least one anode and a plurality of cathodes, the at least one anode including the plurality of x-ray focal spots, and the plurality of collimators being on the at least one anode in the first x-ray tube, or includes a plurality of x-ray tubes, anodes of the plurality of x-ray tubes including the plurality of x-ray focal spots, each respective collimators among the plurality of collimators being on a corresponding anodes in a corresponding x-ray tubes among the plurality of x-ray tubes, and the corresponding anode being among the anodes, the method comprising:

selecting, via a first collimator among the plurality of collimators, the second x-rays, the common detector being common to the plurality of x-ray focal spots.

9. The method of claim 7, wherein the generating of the image data is performed during mammography.

10. The x-ray system of claim 2, wherein a number of the plurality of cathodes is equal to a number of the plurality of x-ray focal spots.

11. The x-ray system of claim 2, each of the plurality of collimators is separate from one another.

12. The x-ray system of claim 3, each of the plurality of collimators is separate from one another.

13. The x-ray system of claim 2, wherein the x-ray source is embodied as the first x-ray tube, the plurality of collimators being on the at least one anode in the first x-ray tube; or the x-ray source is embodied as the plurality of x-ray tubes, each respective collimator among the plurality of collimators being on a corresponding anodes in a corresponding x-ray tubes among the plurality of x-ray tubes, and the corresponding anode being among the anodes.

14. The x-ray system of claim 2, wherein the x-ray source is embodied as the first x-ray tube, the plurality of collimators being attached to an inside of a vacuum casing of the first x-ray tube; or the x-ray source is embodied as the plurality of x-ray tubes, each respective collimator among the plurality of collimators is attached to an inside of a vacuum casing of a corresponding x-ray tube among the plurality of x-ray tubes.

15. The x-ray system of claim 1, wherein the x-ray source is embodied as the first x-ray tube.

16. The x-ray system of claim 1, wherein the x-ray source is embodied as the first x-ray tube; and the plurality of collimators is on the at least one anode in the first x-ray tube.

17. The x-ray system of claim 1, wherein the x-ray source is embodied as the plurality of x-ray tubes; and each respective collimator among the plurality of collimators is on a corresponding anode in a corresponding x-ray tube among the plurality of x-ray tubes, the corresponding anode being among the anodes.

18. The x-ray system of claim 1, wherein the x-ray source is embodied as the first x-ray tube; and the plurality of collimators are attached to an inside of a vacuum casing of the first x-ray tube.

19. The x-ray system of claim 1, wherein the x-ray source is embodied as the plurality of x-ray tubes; and each respective collimator among the plurality of collimators is attached to an inside of a vacuum casing of a corresponding x-ray tube among the plurality of x-ray tubes.

20. The x-ray system of claim 1, wherein the x-ray system is configured to perform tomosynthesis imaging.

* * * * *